United States Patent [19]

Riley et al.

[11] Patent Number: 4,605,517

[45] Date of Patent: Aug. 12, 1986

[54] METHOD OF PREPARING STEROID COMPOUNDS OF CONTROLLED PARTICLE SIZE

[75] Inventors: Derek C. Riley, Tyne and Wear; David Johnston, Newcastle upon Tyne, both of England

[73] Assignee: Sterling Drug Inc., New York, N.Y.

[21] Appl. No.: 659,594

[22] Filed: Oct. 11, 1984

[30] Foreign Application Priority Data

Oct. 29, 1983 [GB] United Kingdom ............... 8328929

[51] Int. Cl.$^4$ .............................................. C07J 43/00
[52] U.S. Cl. ...................................... 540/52; 540/57; 540/79
[58] Field of Search ................... 260/239.55 R, 239.5

[56] References Cited

U.S. PATENT DOCUMENTS

| 4,277,409 | 7/1981 | Warnart et al. | 260/397.45 |
| 4,391,755 | 7/1983 | Wang et al. | 260/397.5 |
| 4,459,235 | 7/1984 | Chenn et al. | 260/397.5 |

FOREIGN PATENT DOCUMENTS 8329173  11/1983  United Kingdom ....... 260/239.55 R

*Primary Examiner*—Elbert L. Roberts
*Attorney, Agent, or Firm*—Theodore C. Miller; Paul E. Dupont; B. Woodrow Wyatt

[57] ABSTRACT

The method of preparing a 2α-cyano-4α,5α-epoxy-3-oxo steroid or a steroid fused at the 2- and 3-positions with a heterocyclic ring of controlled particle size which comprises dissolving the steroid in an organic solvent, precipitating the steroid by mixing a non-solvent for the steroid with the resulting solution, and controlling the time of mixing and the degree of agitation during mixing.

17 Claims, No Drawings

METHOD OF PREPARING STEROID COMPOUNDS OF CONTROLLED PARTICLE SIZE

BACKGROUND OF THE INVENTION

1. Field of the Invention

The invention relates to a method of preparing steroid compounds, in particular compounds requiring a particle size within a specific range.

2. Information Disclosure Statement

In British Application No. 82-31278 filed Nov. 2, 1982, which was refiled as Application No. 83-29173 on November 1, 1983, and corresponding U.S. application Ser. No. 545,810 filed Oct. 26, 1983 (George Margetts, inventor) there are described and claimed, in particular for use in preparing pharmaceutical compositions having improved absorption characteristics, certain 2α-cyano-4α,5α-epoxy-3-oxosteroid compounds, the compounds being in particulate form and consisting of particles having a mean equivalent sphere volume diameter less than about 20 μm, at least 95% of the particles having a particle size of less than about 50 μm.

The earlier applications are particularly concerned with the steroid compound having the common name "trilostane", although the earlier invention also embraces the steroid compound known by the common name "epostane", which is a compound having the formula:

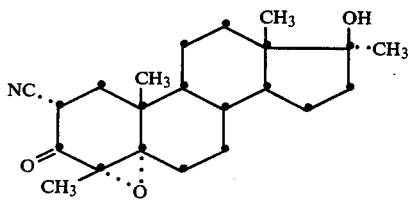

(I)

The earlier applications describe the preparation of, for example, trilostane in particulate form within the specified particle size range by the use of milling, preferably using a fluid energy (air) mill under suitable conditions e.g. of air pressure and feed rate. In the case of epostane, however, we have observed that the raw compound is not easily reduced to a suitable particle size using a milling technique,.and in some instances milling can lead to a polymorphic change which is undesirable, or to the formation of other impurities.

SUMMARY OF THE INVENTION

According to the invention there is provided the method of preparing a compound having a basic ring structure of the general formula:

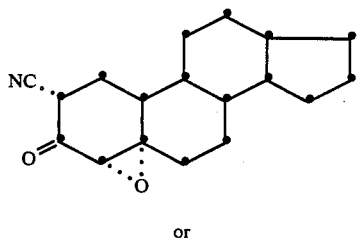

(II)

or

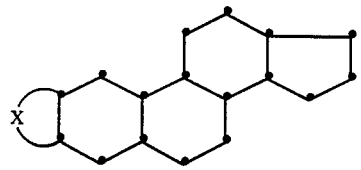

(III)

wherein X represents the remainder of a heterocyclic ring, in particular a 5-membered ring having at least two heteroatoms, in the form of particles having a means equivalent sphere volume diameter less than about 20 μm, at least 95% of the particles having a particles size of less than about 50 μm, or having a specific surface area from about 0.1 to about 10 $m^2g^{-1}$, which method comprises dissolving the compound in an organic solvent, precipitating the compound by mixing an approximately equal volume of a non-solvent for the compound with the resulting solution, and controlling the mixing conditions so that the time of mixing is from about 0.5 to about 30 minutes and the mixture is agitated during mixing.

DETAILED DESCRIPTION OF THE INVENTION INCLUSIVE OF THE PREFERRED EMBODIMENTS

The method of the invention provides steroid compounds in a form comprising particles having a mean equivalent sphere volume diameter less than about 20 μm, at least 95% of the particles having a particle size of less than about 50 μm, preferably of from about 5 to about 12 μm but sometimes outside this range, that is, above 12 μm, e.g. 15 μm, but more generally below 5 μm.

Additionally or alternatively, in the method of the present invention the mixing may be controlled so that the compound is prepared in a form exhibiting a specific surface area of from about 0.1 to about 10 $m^2g^{-1}$. Preferably, the mixing is controlled so that the specific surface area of compounds prepared by the method of the invention is from about 2 to about 4 $m^2g^{-1}$.

While a variety of organic solvents may be employed to dissolve compounds having a basic ring structure of the formula II or III set out above, the preferred organic solvent for use in the method of the present invention is dimethylformamide (DMF). Acetone can also be used. In addition, it is preferred to use water as the non-solvent or a non-solvent comprising water.

In carrying out the method of the invention the desired particle size characteristics are preferably obtained by controlling the rate of mixing of the non-solvent with the solution of the compound to be treated in a suitable organic solvent. Preferably the volume of non-solvent is approximately equal to the volume of solvent and mixing is accomplished over a period of time of from about 4 to about 10 minutes. A typical mixing time is about 6 minutes and the necessary metering of non-solvent may conveniently be effected using a pump, for example, a peristaltic pump to supply the non-solvent to the solution. Alternatively, flow mixing (where the solution and solvent are blended in equal proportions) or inverse addition (where the solution is added to the non-solvent) may be employed.

In the method of the invention it is also preferred that the mixing should be effected under conditions in which at least the solution is agitated, and preferably conditions of high turbulence such as are obtained using a vibro-mixer. The degree of agitation necessary is to some extent governed by the rate of mixing of the non-solvent with the solution, and in order to ensure that a homogeneous mixture is produced it is preferable to increase the degree of agitation as the rate of mixing increases. It is believed the rate of mixing determines the particle size, while the degree of agitation determines the uniformity of the product, i.e. the higher the degree of agitation the more uniform the product. However, provided those criteria are kept in mind the degree of agitation may be varied widely, for example, as represented by stirring speeds of from about 50 to about 500 rpm. Preferably the thus-formed liquid/solid suspension is also stirred out under less turbulent conditions.

While the method of the invention is applicable to a variety of steroid compounds within the above formula II or III the method is particularly applicable to the compounds commonly known as "trilostane" and "epostane", those compounds pounds falling within the formula:

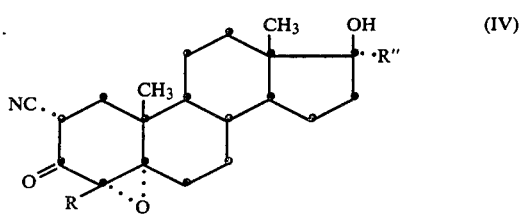

wherein R is hydrogen or methyl and R" is hydrogen or lower alkyk.

In the above formula IV the compound known as "trilostane" is that wherein R and R" are hydrogen, and the compound known as "espostane" is that wherein R and R" are methyl.

Other specific compounds to which the mentod of the invention is applicable are the compound know as "nivacortol" or "nivazol" that is a compound having the formula:

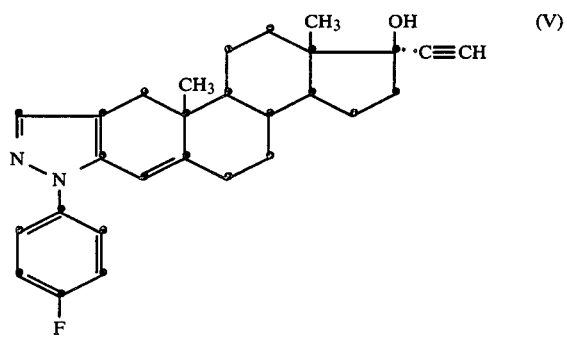

or the compound known as "danazol", that is a compound of the formula:

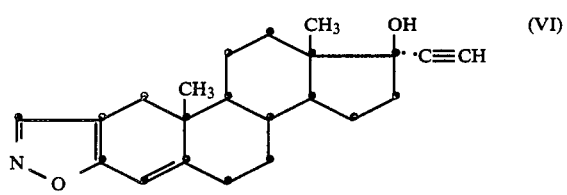

The method of the invention may include the step of isolating the compound prepared in the desired particle size form, as well as one or more additional steps of blending the compound of reduced particle size with one or more pharmaceutically-acceptable excipients or carriers, and optionally thereafter bringing the thus-formed composition into a unit dosage form, for example a tablet, a capsule, a granulate for suspension, a cream, an ointment, a suppository or a suspension. In particular the method of the invention may include the additional steps of granulation and terminal blending subsequent to isolation of the compound of reduced particle size.

The compound prepared in the desired particle size form may be isolated from the solid compound/solvent/non-solvent mixture by, for example, filtration, then washed and dried. A variety of drying techniques may be employed which may include one or more of suction drying, tray drying and oven drying.

The method of the invention and compounds prepared thereby are illustrated in the procedures of the following specific examples.

EXAMPLE 1

3.49 kg of epostane were dissolved in 15 l of Analar brand of DMF at 25° C. under an atmosphere of nitrogen gas to give an almost colourless solution. The solution was passed rapidly through a glass wool plug, in order to remove any undissolved particulate matter, into a 60 l stainless steel container under a blanket of nitrogen gas. The clear solution was rapidly stirred using a glass Herschberg stirrer. 15 l of distilled water were added over a period of 30 seconds and the temperature of the thus-formed liquid/solid suspension rose to 37° C. The suspension was stirred out overnight under a blanket of nitrogen gas and the mixture was cooled to 0° C. using a stainless steel flexiprobe cooler. The product was then recovered by filtration through a polypropylene filter cloth (smooth side facing upwards) on a bench top Buchner funnel and pressed-dry. The product was washed with water (2×12.5 l) at 17° C. and dried under suction for 36 hours. The partially dry material was transferred to large stainless steel trays and dried in air for 5 days. The material was spread out thinly on the trays and the larger lumps of material were broken up at regular intervals (every 6 hours) to assist the drying process. After this time the material was dried in vacuo at 65° C. for 24 hours, the temperature of the vacuum-oven being controlled using a 'fail-safe' Fi-monitor to ensure that the temperature of the vacuum-oven did not exceed 65° C., since overheating of the oven is detrimental to the quality of the product. Yield: 3.13 kg, 89.7%, m.p. 170.4° to 172° C.

The infra-red spectrum, differential scanning calorimeter trace and X-ray powder diffractogram of the thus-prepared material confirmed that the material had the desired polymorphic form (Form I).

Microscopic examination revealed a fairly narrow range of particle sizes up to approximately 15 μm with the vast majority of particles being less than 5 μm. Surface area measurements (Strohlein) gave duplicate values of 8.44 $m^2g^{-1}$ and 7.57 $m^2g^{-1}$.

EXAMPLE 2

A 5.082 kg sample of epostane was divided into two batches of 2.541 kg and each batch was dissolved in 10.92 l of DMF under a flow of nitrogen gas at 60° C. to give a dark brown, almost black coloured solution. When all the epostane had dissolved, the two batches were combined in a large 60 l stainless steel container under a blanket of nitrogen gas. The solution was stirred rapidly by a glass Herschberg stirrer and two Buchi "vibro-mixers" at full power. 21.73 l of water were added over a period of 30 seconds and the final temperature of the thus-formed liquid/solid suspension was 46° C. The "vibro-mixers" were switched off after a uniform suspension was achieved (approx. 30 seconds). The thick, white suspension was stirred out overnight under a blanket of nitrogen gas and the mixture was simultaneously cooled to 0° C. using a stainless steel flexiprobe cooler. The product was recovered by filtration of the suspension through a polypropylene filter cloth (smooth side facing upwards) on a benchtop Buchner funnel and washed with distilled water (60 l) and pressed dry. The product was dried under suction for 24 hours and transferred to stainless steel trays and air-dried at ambient temperature for 5 days. The material was spread out thinly on the trays and the larger lumps of material were broken up at regular intervals (every 6 hours) to assist the drying process. The material was then transferred to a vacuum oven and dried in vacuo at 50° to 60° C. for 36 hours to give a white, very fine crystalline powder of epostane, the temperature of the vacuum-oven again being controlled using a 'fail-safe' Fi-monitor to ensure that the temperature of the vacuum-oven did not exceed 65° C. Yield: 4.91 kg, 97%, m.p. 169.8° to 171.4° C.

Infra-red spectrum and X-ray powder diffractogram data confirmed that the thus-formed epostane is of the desired polymorphic Form I.

Microscopic examination revealed a narrow distribution of particle sizes with the vast majority of particles less than 5 μm in size. Surface area measurements (Strohlein) gave duplicate values of 7.27 $m^2g^{-1}$ and 7.36 $m^2g^{-1}$.

EXAMPLE 3

Effect of Addition Rate on Particle Size

For each of four experiments, epostane (250 g) was dissolved in DMF (1.05 l) at 40° C. in a 2 liter flat-topped reactor under a nitrogen atmosphere and the solution stirred at about 300 rpm by a glass Hershberg stirrer driven by a Citenco overhead mechanical stirrer motor. The solution was allowed to cool within the range of from 30° C. to 35° C. and then water at room temperature (1.05 l) was added over one of the following approximate periods:

0.5 minutes—manually
2 minutes—via peristaltic pump
4 minutes—via peristaltic pump
32 minutes—via peristaltic pump.

The suspensions resulting from the addition of water were stirred for a further hour under nitrogen and then the precipitated material was recovered by filtration. The residues, after washing with water (3 l) were dried under reduced pressure overnight and then in a vacuum oven (approx. 2 mm Hg) at 60° C. for a further 24 hours.

All batches of material produced were shown to be predominantly of the desired end polymorph by means of infra-red spectroscopy and X-ray powder diffraction and all were acceptable analytically. The results of duplicate determinations of the surface areas (Strohlein) of the materials produced are given below:

| Addition time (min) | Surface Area ($m^2g^{-1}$) |
| --- | --- |
| 0.5 | 9.49, 9.80 |
| 2 | 5.34, 5.38 |
| 4 | 3.79, 3.83 |
| 32 | 1.72, 1.48 |

EXAMPLE 4

500 g of epostane were dissolved in DMF (2.1 l) at 40° C. and the solution stirred under nitrogen as described in Example 3 above. Water (2.1 l) at 25.5° C. was added over 6 minutes via a previously calibrated Watson-Marlow 501 Hiflow brand peristaltic pump. After the addition of water was complete, the suspension was stirred for a further hour. The epostane recovered by filtration through a polypropylene cloth was washed carefully with 6 liters of water. The filter cake was dried under suction overnight and then transferred to a vacuum oven where it was dried in vacuo (2 mm Hg) for 4 hours at ambient temperatures and 16 hours at 60° C.

The yield of the white crystalline product was 479 g (96%).

Duplicate values of 3.11 $m^2g^{-1}$ and 3.17 $m^2g^{-1}$ (Strohlein) were obtained on the material produced.

EXAMPLE 5

2.1 kg of epostane were placed in a 20 l flat top reactor, fitted with thermometer, nitrogen bleed and a Citenco overhead mechanical stirrer. DMF (8.82 l) preheated to 40° C. was added to the reactor under a blanket of nitrogen gas. The mixture was stirred at 300 rpm until all the epostane had dissolved (3 to 4 minutes). The temperature of the DMF solution was 34.5° C. Water at 27.5° C. was added at a rate of 1.47 l min$^{-1}$ for 6 minutes.

Crystallization commenced after 2.25 minutes. After the water addition was complete, the liquid/solid suspension was stirred out for 1 hour under a blanket of nitrogen gas.

The epostane was recovered by filtration on a polypropylene filter cloth (smooth surface upwards) and washed well with distilled water (1×20 l, 1×12 l, 2×4 l). The material was dried under suction overnight and then transferred to stainless steel trays and air-dried for 3 days and finally dried under vacuum ($\leq$2mm Hg) at 60° C. for 16 hours.

Two further batches of 2.1 kg and 1 kg were also processed as described above.

The three products thus-obtained were all of the desired polymorphic form, all had surface areas (Strohlein) in the range 3.1 to 3.3 $m^2g^{-1}$ and recoveries ranged from 92 to 95.4%.

EXAMPLE 6

The method of the invention was carried out using the compound of formula V as the steroid, acetone as the solvent and water as the non-solvent. The following results were obtained.

| Addition Time (min) | Surface Area ($m^2g^{-1}$) |
| --- | --- |
| 0.5 | 0.42 |
| 2 | 0.52 |
| 4 | 0.37 |
| 8 | 0.45 |

| Addition Time (min) | Surface Area (m²g⁻¹) |
|---|---|
| 16 | 0.35 |

EXAMPLE 7

The method of the invention was carried out using 2α-cyano-4α,5α-epoxyandrostan-3,17-dione as the steroid, DMF as the solvent and water as the non-solvent. The following results were obtained.

| Addition Time (min) | Surface Area (m²g⁻¹) |
|---|---|
| 0.5 | 5.48 |
| 2 | 4.86 |
| 4 | 5.38 |
| 8 | 3.34 |
| 16 | 4.28 |

We claim:

1. The method of preparing a compound having a basic ring structure of the general formula:

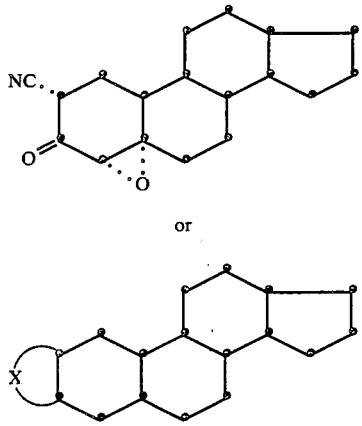

(II)

or (III)

wherein X represents the remainder of a heterocyclic ring, in particular a 5-membered ring having at least two heteroatoms, in the form of particles having a means equivalent sphere volume diameter less than about 20 μm, at least 95% of the particles having a particle size of less than about 50 μm, or having a specific surface area from about 0.1 to about 10 m²g⁻¹, which method comprises dissolving the compound in an organic solvent, precipitating the compound by mixing an approximately equal volume of a non-solvent for the compound with the resulting solution, and controlling the mixing conditions so that the time of mixing is from about 0.5 to about 30 minutes and the mixture is agitated during mixing.

2. The method according to claim 1 wherein the mixing is controlled so that the compound is prepared in a form consisting of particles having an equivalent sphere volume diameter of from about 5 to about 12 μm.

3. The method according to claim 1 wherein the mixing is controlled so that the specific surface area of the precipitated compound is from about 2 to about 4 m²g⁻¹.

4. The method according to claim 1 wherein the organic solvent is dimethylformamide.

5. The method according to claim 1 wherein the nonsolvent is water.

6. The method according to claim 1 wherein a volume of non-solvent approximately equal to the volume of solvent is mixed with the solution over a period of time of about 4 to about 10 minutes.

7. The method according to claim 6 wherein the mixing time is about 6 minutes.

8. The method according to claim 1 wherein the nonsolvent is metered into the solution using a pump.

9. The method according to claim 1 wherein the compound is one having the formula:

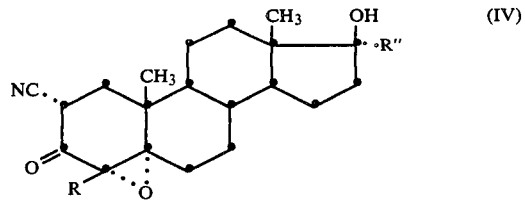

(IV)

wherein R is hydrogen or methyl and R" is hydrogen or lower alkyl.

10. The method according to claim 9 wherein R and R" are methyl.

11. The method according to claim 9 wherein R and R" are hydrogen.

12. The method according to claim 1 wherein the compound is one having the formula:

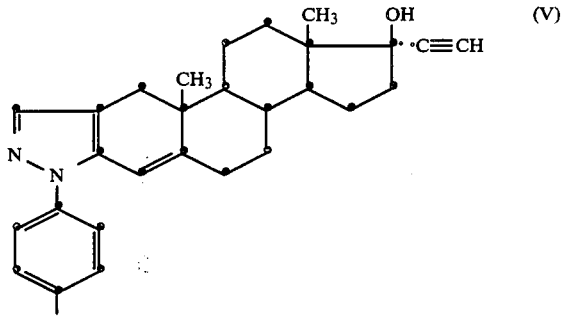

(V)

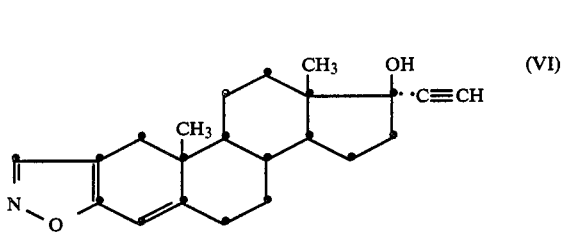

(VI)

13. The method according to claim 1 which includes the additional step of isolating the compound prepared in the desired particle size form, and the isolation includes one or more drying steps selected from suction drying, tray drying and oven drying.

14. The method according to claim 13 which includes one or more additional steps of blending isolated compound of reduced particle size with one or more pharmaceutically-acceptable excipients or carriers.

15. The method according to claim 14 wherein the blended compound is brought into a unit dosage form.

16. The method according to claim 15 wherein the blended compound is formulated as a tablet, a capsule, a granulate for suspension, a cream, an ointment, a suppository or a suspension.

17. The method according to claim 14 which includes the additional steps of granulation and terminal blending subsequent to isolation of the compound of reduced particle size.

* * * * *